United States Patent [19]

Bender et al.

[11] Patent Number: 4,778,806

[45] Date of Patent: Oct. 18, 1988

[54] INHIBITION OF INTERLEUKIN-1 PRODUCTION BY MONOCYTES AND/OR MACROPHAGES

[75] Inventors: Paul E. Bender, Cherry Hill, N.J.; Don E. Griswold, North Wales, Pa.; Nabil Hanna, Berwyn, Pa.; John C. Lee, Radnor, Pa.

[73] Assignee: SmithKline Beckman Corporation, Philadelphia, Pa.

[21] Appl. No.: 898,447

[22] Filed: Aug. 19, 1986

[51] Int. Cl.$^4$ .............................................. A61K 31/44
[52] U.S. Cl. .................................................... 514/336
[58] Field of Search ................ 530/395; 514/397, 825, 514/885, 333, 336; 548/336, 335

[56] References Cited

U.S. PATENT DOCUMENTS 4,188,397  2/1980  Hill ...................................... 514/397

OTHER PUBLICATIONS

Stites, D. P., Stobo, J. D., Fudenberg, H. H., and Wells, J. V., Basic and Clinical Immunology, Lange Medical Publications, Los Altos, Calif., 1984, p. 90.
Ser. No. 856,735, Apr. 28, 1986, Bender et al.

*Primary Examiner*—Stanley J. Friedman
*Attorney, Agent, or Firm*—Carol G. Canter; Edward T. Lentz; Alan D. Lourie

[57] ABSTRACT

A method of inhibiting the production of interleukin-1 by monocytes and/or macrophages in a human in need thereof which comprises administering to such human an effective interleukin-1 production inhibiting amount of a 2-2'-[1,3-propan-2-onediyl-bis(thio)]bis-1H-imidazole or a pharmaceutically acceptable salt thereof.

10 Claims, No Drawings

INHIBITION OF INTERLEUKIN-1 PRODUCTION BY MONOCYTES AND/OR MACROPHAGES

BACKGROUND OF THE INVENTION

This invention relates to a method of inhibiting the production of interleukin-1 by monocytes and/or macrophages in a human in need thereof which comprises administering to such human an effective, interleukin-1 production inhibiting amount of a 2-2'-[1,3-propan-2-onediyl-bis(thio)]bis-1H-imidazole or a pharmaceutically acceptable salt thereof, Hill, U.S. Pat. No. 4,188,397, issued Feb. 12, 1980 discloses compounds of the formula

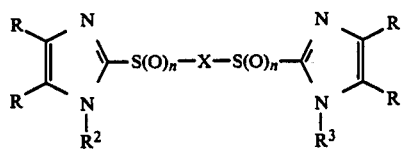

wherein:

R is 4-monosubstituted phenyl wherein said substituent is selected from methoxy, methylthio, trifluoromethyl, chloro, fluoro, bromo or methylenedioxy when taken with an adjacent position on the phenyl ring;

$R^2$ and $R^3$ are both H or one is H and the other is $CH_3$; n is 0, 1 or 2; and X is, among others, $CH_2C(O)CH_2$.

Hill also discloses that such compounds are useful as antiarthritic agents, as confirmed by their ability to inhibit adjuvant induced polyarthritis in rats; and are also useful to regulate cell mediated immunity, as confirmed by the oxazolone-induced contact sensitivity test procedure which measures changes in mouse paw edema produced by administration of test compounds.

The adjuvant-induced polyarthritis assay in rats is useful in detecting compounds which are inhibitors of prostanoid synthesis, mediated by the prostanoids formed by the enzyme cyclooxygenase, but is of no known utility in detecting or suggesting compounds which are inhibitors of interleukin-1 (IL-1) production by monocytes and/or macrophages. The oxazolone-induced contact sensitivity test in which mouse paw volume is measured is useful in detecting compounds which are immunostimulatory, but is of no known utility in detecting or suggesting compounds which are inhibitors of IL-1 production by monocytes and/or macrophages.

SUMMARY OF THE INVENTION

This invention relates to a method of inhibiting the production of Interleukin-1 (IL-1) by monocytes and/or macrophages in a human in need thereof which comprises administering to such human an effective, IL-1 production inhibiting amount of a compound of the formula Formula (I)

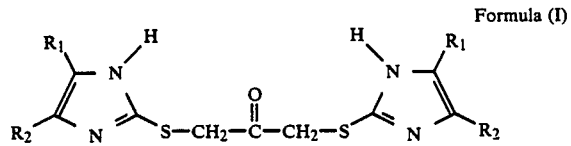

wherein:

one of $R^1$ and $R^2$ is 4-pyridyl and the other is monohalo-substituted phenyl;

or a pharmaceutically acceptable salt thereof.

DETAILED DESCRIPTION OF THE INVENTION

The preparation of all compounds of Formula (I) and pharmaceutically acceptable salts thereof is disclosed in Bender et al., U.S. patent application Ser. No. 856,735, filed Apr. 28, 1986, the disclosure of which is hereby incorporated by reference.

By the term "inhibiting the production of IL-1" is meant the down-regulation of excessive in vivo IL-1 levels in a human to normal levels.

By the term "production of IL-1 by monocytes and/or macrophages" is meant the in vivo release of IL-1 by such cells.

Interleukin-1 (IL-1) has been recently demonstrated to mediate a variety of biological activities thought to be important in immunoregulation and other physiological conditions such as inflammation [See, e.g., Dinarello et al., Rev. Infect. Disease, 6, 51 (1984)].

The myriad of known biological activities of IL-1 include the activation of T helper cells, induction of fever, stimulation of prostaglandin or collagenase production, neutrophil chemotaxis, induction of acute phase proteins and the suppression of plasma iron levels. However, much remains to be learned about the synthesis, processing and secretion of IL-1. For example, there is recent evidence suggesting that there are two separate human interleukin-1 genes, and that the products of these two genes differ in their isoelectric points. It is also clear that the published data on the cloning of the cDNA of the IL-1 gene(s) suggest that IL-1 is synthesized as a 31 Kilodalton (Kd) precursor, which is subsequently processed to yield a smaller mature protein of about 17 Kd, the activity of which is detectable in culture supernatants. One interesting feature of the precursor protein is that it lacks a classical signal peptide sequence, suggesting that the molecule is probably not secreted in a classical manner. There is very little information available as to how the 31 Kd precursor is processed and secreted.

The discovery of a compound which specifically inhibits IL-1 production will not only contribute to the understanding of how this molecule is synthesized, processed and secreted, but will also provide a therapeutic approach for diseases in which excessive or unregulated IL-1 production is implicated.

It has now been discovered that compounds of Formula (I) and pharmaceutically acceptable salts thereof are useful for inhibiting the production of IL-1 by monocytes and/or macrophages in a human in need of such inhibition.

There are several disease states in which excessive or unregulated IL-1 production by monocytes and/or macrophages is implicated in exacerbating and/or causing. These include rheumatoid arthritis [See, e.g., Fontana et al., Arthritis Rheum., 22, 49–53 (1982)]; osteoarthritis [See, e.g., Wood et al., Arthritis Rheum., 26, 975 (1983)]; toxic shock syndrome [See, e.g., Ikejima and Dinarello, J. Leukocyte Biology, 37, 714 (1985)]; other acute or chronic inflammatory disease states such as the inflammatory reaction induced by endotoxin [See, e.g., Habicht and Beck, J. Leukocyte Biology, 37, 709 (1985)]; and other chronic inflammatory disease states such as tuberculosis [See, e.g., Chesque et al., *J. Leukocyte Biology*, 37, 690 (1985)].

Benjamin et al., "Annual Reports in Medicinal Chemistry-20", Chapter 18, pages 173-183 (1985), Academic Press, Inc., disclose that excessive IL-1 production is implicated in psoriatic arthritis, Reiter's syndrome, rheumatoid arthritis, osteoarthritis, gout, traumatic arthritis, rubella arthritis and acute synovitis.

Dinarello, *J. Clinical Immunology*, 5(5), 287-297 (1985), reviews the biological activities which have been attributed to IL-1, and such activities are summarized in Table A.

TABLE A

Biological activities attributed to IL-1

Fever (in rabbits, mice and rats)
Hypoferremia
Hypozincemia
Hypercupremia
Increased
    Blood neutrophils
    Hepatic acute-phase proteins
    Bone resorption
    Cartilage breakdown
    Muscle proteolysis
    Slow-wave sleep
    Endothelial procoagulant
    Chondrocyte proteases
    Synovial collagenase
    Endothelial neutrophil adherence
    Neutrophil degranulation
    Neutrophil superoxide
    Interferon production
Proliferation of
    Fibroblasts
    Glial cells
    Mesangial cells
    Synovial fibroblasts
    EBV B-cell lines
Chemotaxis of
    Monocytes
    Neutrophils
    Lymphocytes
Stimulation of $PGE_2$ in
    Hypothalamus
    Cortex
    Skeletal muscle
    Dermal fibroblast
    Synovial fibroblast
    Chondrocyte
    Macrophage/monocyte
    Endothelium ($PGI_2$)
Decreased
    Hepatic albumin synthesis
    Appetite
    Brain binding of opioids
Augmentation of
    T-cell responses
    B-cell responses
    NK activity
    IL-2 production
    Lymphokine production An effective, IL-1 production inhibiting amount of a compound of Formula (I) or a pharmaceutically acceptable salt thereof is useful in treating, prophylactically or therapeutically, any disease state in a human which is exacerbated or caused by excessive or unregulated IL-1 production by such human's monocytes and/or macrophages.

This invention relates to a method of inhibiting the production of IL-1 by monocytes and/or macrophages in a human in need thereof which comprises administering an effective, IL-1 production inhibiting amount of a compound of Formula (I) or a pharmaceutically acceptable salt thereof to such human. A compound of Formula (I) or a pharmaceutically acceptable salt thereof can be administered to such human in a conventional dosage form prepared by combining a compound of Formula (I) or a pharmaceutically acceptable salt thereof with a conventional pharmaceutically acceptable carrier or diluent according to known techniques such as those described in Bender et al., U.S. Ser. No. 856,735, filed Apr. 28, 1986. It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt thereof is administered to a human in need of inhibition of IL-1 production by its monocytes and/or macrophages in an amount sufficient to inhibit such IL-1 production down to normal levels. The route of administration may be oral, parenteral or topical. The topical dosage regimen wil preferably be from about 2 mg to about 10 mg per site of administration. The daily oral dosage regimen is preferably from about 5 to about 100 mg/kg of total body weight. The term parenteral as used herein includes intravenous, intramuscular, subcutaneous intranasal, intrarectal, intravaginal or intraperitoneal administration. The intravenous and intramuscular forms of parenteral administration are generally preferred. The daily parenteral dosage regimen will preferably be from about 2 to about 100 mg per kilogram (kg) of total body weight, most preferably from about 3 to about 60 mg/kg. It will be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable acid addition salt thereof given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

Inhibitory Effect of a Compound of Formula (I) on in vitro IL-Production By Human Monocytes The inhibitory effect of a compound of Formula (I) on in vitro IL-1 production by human monocytes was determined by the following method: Bacterial lipopolysaccharide (LPS) was used to induce IL-1 production by human peripheral blood monocytes. IL-1 activity was measured by its ability to stimulate a Interleukin 2 (IL-2) producing cell line (EL-4) to secrete IL-2, in concert with A23187 ionophore, according to the method of Simon et al., *J. Immunol. Methods,* 84, 85-94 (1985). Human peripheral blood monocytes were isolated and purified from either fresh blood preparations from volunteer donors, or from Blood Bank buffy coats, according to the procedure of Colotta et al., *J. Immunol.,* 132,936 (1984).

$1 \times 10^6$ human peripheral blood monocytes [isolated and purified from either fresh blood preparations from volunteer donors, or from blood bank buffy coats, according to the method of Colotta et al., *J. Immunol.,* 132, 936 (1984)]were plated in 24-well plates at a concentration of 2 million/ml per well, and allowed to adhere for 1 hour (hr) at 37° C. The compound of Formula (I) was added to a final concentration of $10^{-5}$M to $10^{-8}$M. The monocytes were stimulated to produce IL-1 with 10 ng/ml LPS after a 1 hr pretreatment of the cells with the respective compounds. The cultures were incubated at 37 C for an additional 24 hours, and then culture supernatants were removed and clarified of cells and all debris, and were immediately assayed for IL-1 biological activities by radioimmunoassay.

The results indicated that human peripheral blood monocytes are exquisitely sensitive to bacterial endotoxin (LPS). Nanogram or even picogram quantities of LPS stimulated high levels of IL-1 production.

In this assay, ibuprofen, a highly active inhibitor of prostaglandin synthesis, had virtually no effect on IL-1 production at concentrations of $10^{-5}$M, $10^{-6}$M and $10^{-7}$M and the 5-lipoxygenase inhibitors phenidone and nordihydroquaiaretic were only marginally active in the inhibition of IL-1 production at a concentration of $10^{-6}$M.

Table 1 summarizes the results obtained with Formula (I) compounds and shows that compounds of Formula (I) inhibit IL-1 production.

TABLE 1

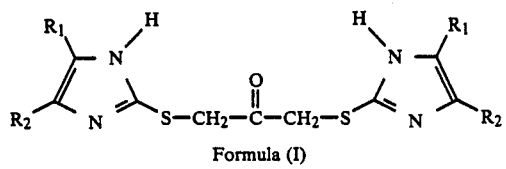

Formula (I)

| Compound No. | $R_1$ | $R_2$ | % Inhibition @ $10^{-6M}$ |
|---|---|---|---|
| 1 | 4-pyridyl | 4-fluorophenyl | 63 |

Based on the widely held belief of the role of unmodulated (i.e., excessive) in vivo IL-1 production in causing or aggravating inflammatory responses and other disease states (See, e.g., Fontana et al., supra; Wood et al., supra; Ikejima and Dinarello, supra; Habicht and Beck, supra; Chesque et al., supra; Benjamin et al., supra and Dinarello, supra), and based on the fact that compounds of Formula (I) inhibit in vitro IL-1 production by human macrophages and/or monocytes (see, Table I), it is expected that all compounds of Formula (I) inhibit the in vivo IL-1 production by monocytes and/or macrophages in a human in need thereof when used according to the method of the subject invention.

What is claimed is:

1. A method of inhibiting the production of interleukin-1 by monocytes and/or macrophages in a human in need thereof which comprises administering to such human an effective, interleukin-1 production inhibiting amount of a compound of the formula:

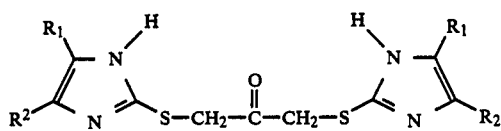

wherein:
one of $R^1$ and $R^2$ is 4-pyridyl and the other is monohalo-substituted phenyl;
or a pharmaceutically acceptable salt thereof.

2. The method of claim 1 wherein the route of administration is parenteral.

3. The method of claim 2 wherein the route of administration is intravenous or intramuscular.

4. The method of claim 3 wherein the amount of compound is administered on a daily dosage regimen of from about 2 to about 100 mg per kg of total body weight.

5. The method of claim 4 wherein the daily dosage regimen is from about 3 to about 60 mg per kg of total body weight.

6. The method of claim 1 wherein the route of administration is topical.

7. The method of claim 6 wherein the amount of compound administered is from about 2 mg to about 10 mg per site of administration.

8. The method of claim 1 wherein the administration is oral.

9. The method of claim 8 wherein the amount of compound administered is from about 5 to about 100 mg/kg of total body weight.

10. The method of claim 1 wherein $R^1$ is 4-pyridyl and $R^2$ is 4-fluorophenyl.

* * * * *